United States Patent [19]
Harrold

[11] Patent Number: 5,396,906
[45] Date of Patent: Mar. 14, 1995

[54] BACK SUPPORT BELT

[76] Inventor: David W. Harrold, 22167 Maretlla Ave., Boca Raton, Fla. 33433

[21] Appl. No.: 930,093

[22] Filed: Aug. 13, 1992

[51] Int. Cl.[6] ............................ A61F 5/37; A61F 5/00
[52] U.S. Cl. ........................................ 128/876; 602/19
[58] Field of Search .............. 602/5, 13, 19; 128/878, 128/876, DIG. 10, 96.1

[56] References Cited

U.S. PATENT DOCUMENTS

| | | | |
|---|---|---|---|
| 1,646,590 | 10/1927 | Mildenberg. | |
| 2,240,308 | 4/1941 | Mahe | 128/96 |
| 2,427,546 | 9/1947 | Brooks | 128/118 |
| 2,720,202 | 10/1955 | Thompson | 128/101 |
| 3,052,236 | 9/1962 | Schrieber | 128/78 |
| 3,071,133 | 12/1960 | Eisen | 128/78 |
| 4,135,503 | 1/1979 | Romano | 128/78 |
| 4,178,922 | 12/1979 | Curlee | 602/13 |
| 4,178,923 | 12/1979 | Curlee | 128/78 |
| 4,552,135 | 11/1985 | Racz | 602/13 |
| 4,622,957 | 11/1986 | Curlee | 128/78 |
| 4,802,667 | 2/1989 | Altner | 272/123 |
| 4,817,595 | 4/1989 | Maass | 128/155 |
| 4,993,409 | 2/1991 | Grim | 128/78 |
| 5,195,948 | 3/1993 | Hill et al. | 602/19 |

*Primary Examiner*—Michael A. Brown
*Attorney, Agent, or Firm*—Senniger, Powers, Leavitt & Roedel

[57] ABSTRACT

A back support belt having inflatable bladder members mounted on the inner surface of the belt to engage and support the lower back. A pump is further provided for inflating and deflating the bladder. The pump is integrally attached to the belt and includes a valve operable to permit inflation and deflation of the bladder, and a conduit for fluid communication between the pump, valve and the bladder.

8 Claims, 1 Drawing Sheet

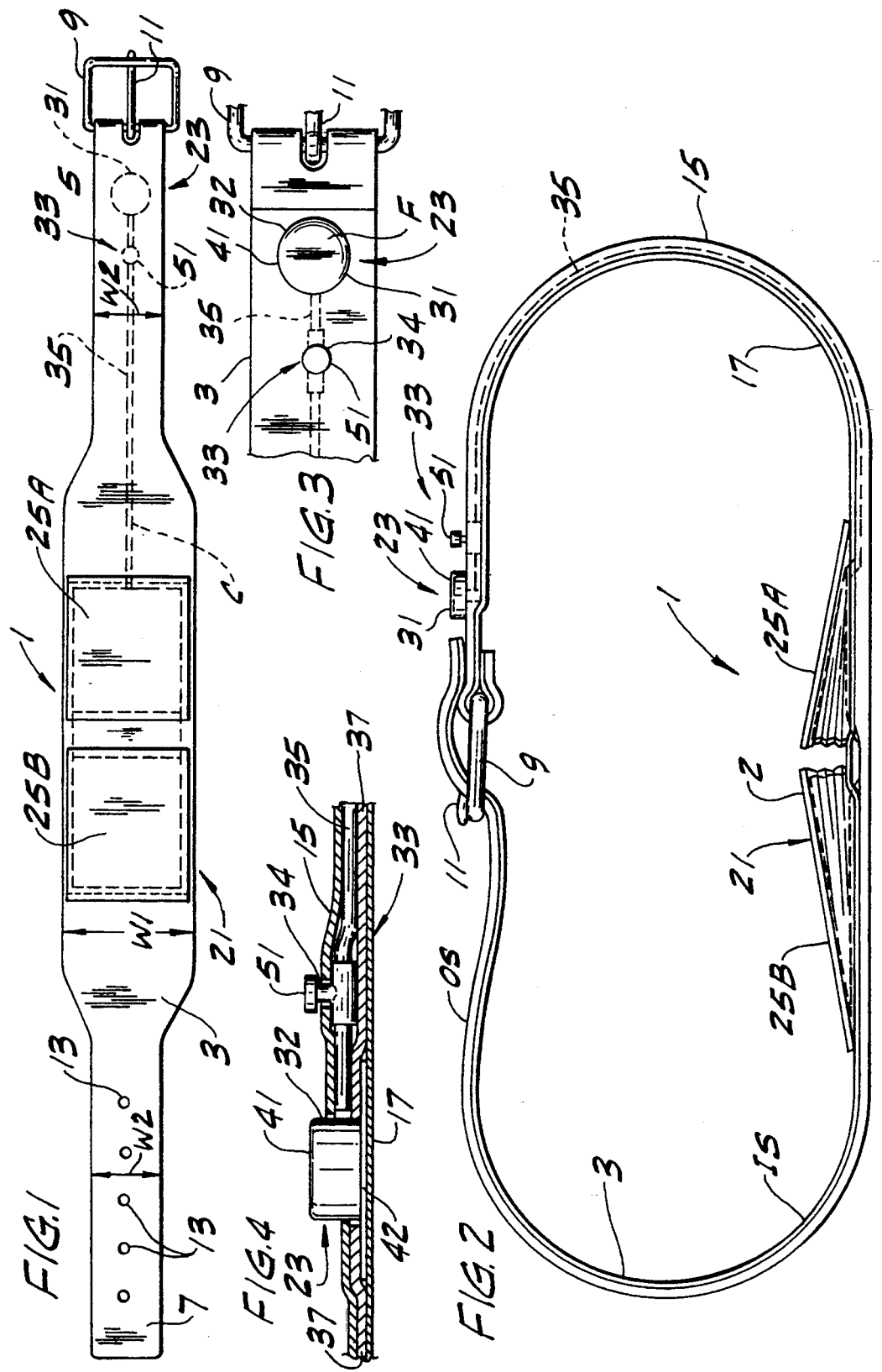

BACK SUPPORT BELT

BRIEF SUMMARY OF THE INVENTION

This invention relates generally to belts, and more particularly to a back support belt capable of fitting around the waist of a human body for supporting the lower back.

The invention involves improvements for facilitating the inflation of an inflatable bladder of a back support belt, such as those used by weightlifters. Reference may be made generally to U.S. Pat. Nos. 1,646,590, 4,135,503, 4,178,923 and 4,622,957 disclosing belts having inflatable bladders of various shapes and sizes positioned against the lower back of its wearer. The back support belts shown in these references typically consist of a belt, inflatable bladders affixed to the belt at various locations along the length of the belt, and an inflator for filling the inflatable bladders with air. In each these references, the inflator is a large squeeze bulb located externally from the belt. In weightlifting, for example, it is desirable that the inflator is located out of the way so that it does not interfere with the activities performed by its wearer.

Among the several objects of this invention may be noted the provision of an improved back support belt which provides greater support to the lower back of a wearer; tile provision of such an improved back support belt having an inflatable bladder for providing variable support depending upon the amount of support required by its wearer; the provision of such an improved back support belt having an inflatable bladder which is easily inflated and deflated; the provision of such a back support belt having an inflator integral with the belt so that it is out of the way during use of the belt; and the provision of such a back support belt which is durable, simple in construction and easy to use.

Generally, a back support belt of this invention comprises back support means mounted on the inner surface of the belt comprising an inflatable bladder adapted to engage and support the lower back. Bladder inflation means is further provided for inflating and deflating the bladder. The bladder inflation means comprises a pump integrally attached to the belt, a valve operable to permit inflation and deflation of the bladder, and conduit means for fluid communication between the pump, valve and the bladder.

In one aspect of the invention the bladder comprises two spaced-apart inflatable bladder members mounted on the belt so that one bladder member is engageable with the lower back on one side of the spine and the second bladder member is engageable with the lower back on the opposite side of the spine. Each bladder member is generally wedge-shaped upon its inflation, with the thickest portion of the wedge disposed generally adjacent the spine and the thinnest portion of the wedge disposed laterally outwardly of the spine.

Other objects and features will be in part apparent and in part pointed out hereinafter.

BRIEF DESCRIPTION OF THE DRAWINGS

FIG. 1 is a front view of a back support belt of the present invention with the belt in its open loop position;

FIG. 2 is a plan of the back support belt shown in FIG. 1 with the belt in its closed loop position;

FIG. 3 is an enlarged fragmentary front view of a bladder inflator for inflating and deflating a bladder; and FIG. 4 is an enlarged fragmentary plan view of the bladder inflator.

Corresponding parts are designated by corresponding reference numerals in the several views of the drawings.

DESCRIPTION OF THE PREFERRED EMBODIMENT

Referring now to the drawings, and particularly to FIGS. 1 and 2, there is generally indicated at 1 a back support belt of the present invention which is capable of fitting around the waist of a human body (not shown). Support belt 1 comprises an elongate nylon or leather strap 3 forming the body of the belt. Generally, strap 3 is of standard construction, such as those found for weight lifting, and is configured such that the middle of the belt is of consistent width W1 for in part supporting the lower back of a wearer. The strap tapers to a narrower width W2 at each end 5, 7 at the portion of the strap not in contact with the lower back of its wearer. However, it is to be understood that the width of the belt, and the material from which it is made, may vary and still fall within the scope of the present invention.

At the one end 5 of the strap, there is a buckle 9 having a tongue 11 which is selectively receivable through one of a plurality of openings 13 in the opposite end 7 of the belt to secure the belt around the wearer's waist. The strap 3 may have other suitable connectors for use in securing the belt around the wearer's waist and still fall within the scope of the present invention. For instance, velcro (not shown) may be attached to the outer surface OS of the belt at end 7 so that it is secured about the waist by slipping the end 7 through the buckle 9, folding the end 7 over and securing it to itself. Strap 3 has an outer layer 15 preferably made from nylon, and an inner layer 17 which may be made from leather. However, the scope of the present invention includes materials other than nylon and leather. The inner layer 17 has an inner surface IS which contacts the lower back and provides support thereto.

An inflatable bladder (broadly back support means), generally indicated at 21, is mounted on the inner surface IS of the strap 3 and is engageable with, and, along with the wide portion W1 of the strap, helps support the lower back. Means for inflating the bladder, indicated generally at 23, inflates and deflates the inflatable bladder 21 with air. In its most preferred embodiment, there is one bladder having two bladder members 25A, 25B which are spaced apart as shown in FIGS. 2 and 3, and are connected to one another through a common passageway located between the two members. The bladder members 25A, 25B are mounted on the strap 3 generally centrally on the wider portion W1 of the strap so that one bladder member 5A is engageable with the lower back on one side of the wearer's spine and the second member 25B is engageable with the lower back on the opposite side of the spine. As best shown in FIG. 2, the bladder members 25A, 25B are generally wedge-shaped upon being inflated with air, with the thickest portion of the wedge disposed adjacent the spine and the thinnest portion of the wedge tapering away from and disposed laterally outwardly of the spine. In their shown configuration, each bladder 25A, 25B is rectangular in shape and approximately 3½ to 4 inches in width by 5 to 5½ inches in length. The bladders 25A, 25B are centrally located on the inner surface IS of strap 3 and spaced approximately 1½ to 2 inches apart to allow for the spine positioned therebetween. Preferably, the belt is to be worn around the most narrow part of the wearer's waist right above tile hips. It has been found that this configuration provides the greatest support to the lower back of a person wearing the belt by filling any gaps or spaces naturally occurring between the strap 3 and the waist of the wearer.

Generally, bladder inflation means 23 comprises a pump 31 located adjacent the buckle 9, a valve 33 positioned next to the pump and operable to permit inflation and deflation of the bladder members 25A 25B and a second conduit 35, having a flow passage therethrough, for fluid communication of air between the pump, valve and bladder. Pump 31 is integrally attached to strap 3 so that it is out of the way of the wearer and does not become damaged during normal use of the belt. Portions of bladder inflation means 23 are embedded in the strap in channels C formed between outer and inner layers 15, 17, while other portions (e.g., the face F of pump 31) are exposed so that the wearer may access them. More specifically, two generally circular openings 32, 34 are provided in the outer layer 15 through which the face F of the pump 31 and an air release cap 51, respectfully, protrude. Padding 37, disposed between layers 15, 17, protects the pump, the conduit 35 and the valve 33 from unwanted pressure as the belt is wrapped about the user's waist. As shown, opening 32 is larger than opening 34. Conduit 35 is connected to the bladder members 25A, 25B at bladder member 25A.

Pump 31 comprises an air impermeable, resilient bulb 41 capable of holding air integrally joined to the belt. The pump 31 is movable between a relaxed configuration in which the bulb 41 encloses a maximum volume filled with air, and a collapsed configuration in which the enclosed volume is reduced and air is forced through the valve 33 into the second conduit 35 and finally into the bladder members 25A, 25B. Air is forced out of bulb 41 by manually pressing the bulb (e.g., with a finger) on its face F, thereby collapsing the bulb from its relaxed configuration and moving it to its collapsed configuration. Upon releasing the bulb 41 (e.g., removing the finger from face F), air is drawn back into tile bulb due to a vacuum created by the bulb returning to its relaxed configuration. As shown in FIG. 4, the bulb 41 is attached to flexible sheet material base 42 (e.g., rubber) which is held in place by layers 15, 17 and padding 37.

The valve 33 is a one-way valve which only allows air to flow in a direction from the pump 31 to towards tile bladder members 25A, 25B. However, the release cap 51 is selectively operable to allow air to escape from the bladders. The release cap is located between pump 31 and the bladder members 25A, 25B anywhere along second conduit 35 and projects through the opening 34 provided in outside layer 15. For convenience purposes, release cap 51 is located adjacent pump 31 so that it is easily accessible. By pressing the release cap 51 (e.g., with a finger), air escapes from bladder members 25A, 25B through the second conduit 35 out of an opening (not shown) formed in the release cap. After the release cap 51 is released, the opening is closed, thereby capturing any air left in the bladder members, conduits, or pump.

In use, the belt 1 is positioned around the waist of a wearer such that the bladder members 25A, 25B are positioned against the lower back of the wearer with one bladder member 25A engaging tile lower back on one side of the wearer's spine and the second member 25B engaging the lower back on the opposite side of the spine. The belt is secured to the wearer by slipping the end 7 through the buckle 9 and inserting the tongue 11 into any of the openings 13 provided for at the end 7 of the strap 3. Or alternatively, the end 7 (having velcro material provided on the outside surface thereof) is slipped into the buckle and tightened around the waist and is then secured thereto by the velcro. After belt 1 is tightened about the waist, by continuously pressing pump 31, air is pumped into the bladder members 25A, 25B through valve 33 and second conduit 35 until the wearer determines that the belt has a tight fit about the waist. Essentially, bladder members 25A, 25B fill spaces naturally occurring between the strap 3 and the contour of the body. Air is then removed from the bladders by pressing the release cap 51.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A back support belt comprising:
   an outer layer;
   an inner layer generally superposed with the outer layer, the outer and inner layers being sized and shaped for extending around the waist of a human body;
   means for attaching opposite ends of the belt for securing the belt around the waist;
   inflatable bladder means adapted to be disposed generally opposite the lower back of the human body for providing support to the lower back upon inflation of said bladder means;
   a pump comprising a base and a hollow bulb extending from the base, the base being sandwiched between the inner and outer layers of the belt and being secured to the belt for holding the pump in place, the bulb protruding from between the layers through an opening in the outer layer and being movable between a relaxed configuration in which the bulb encloses a first volume of air and a collapsed configuration in which the bulb encloses a second volume of air smaller than the first;
   conduit means located between the inner and outer layers and extending from the bulb to said inflatable bladder means;
   a valve disposed generally in said conduit means operable to permit fluid communication as the bulb is moved toward its collapsed position to force air from the bulb into said inflatable bladder means.

2. A belt as set forth in claim 1 wherein said valve is located adjacent the bulb and has an operating member protruding through an opening in the outer layer for selectively releasing air from the bladder.

3. A belt as set forth in claim 2 wherein the valve only allows air to flow in a direction from the pump towards the bladder.

4. A belt as set forth in claim 2 wherein the inner and outer layers are elongated and the pump is spaced from said inflatable bladder means.

5. A belt as set forth in claim 1 wherein the bladder comprises two spaced-apart bladder members for supporting the lower back, said bladder members being located on the belt so that one bladder member is engageable with the lower back on one side of the spine for providing support thereto and the second bladder member is engageable with the lower back on the opposite side of the spine.

6. A belt as set forth in claim 5 wherein each bladder member is generally wedge-shaped upon inflation thereof, with the thickest portion of the wedge disposed generally adjacent the spine and the thinnest portion of the wedge disposed laterally outwardly of the spine.

7. A belt as set forth in claim 1 wherein the pressure of the inflatable bladder means when filled with air is above atmospheric air pressure.

8. A back support comprising:

a belt comprising an inner layer having an inner surface for contacting the body and an outer layer;

means for attaching opposite ends of the belt around the waist of a human body;

inflatable bladder means located on the inner surface of the belt comprising an inflatable bladder adapted to engage and support the lower back, the bladder having two spaced-apart inflatable bladder members for supporting the lower back, the bladder members being located on the belt so that one bladder member is engageable with the lower back on one side of the spine for providing support thereto and the second bladder member is engageable with the lower back on the opposite side of the spine, each bladder member being generally wedge-shaped upon inflation thereof, with the thickest portion of the wedge disposed generally adjacent the spine and the thinnest portion of the wedge disposed laterally outwardly of the spine; and a pump comprising a base and a hollow bulb extending from the base, the base being sandwiched between the inner and outer layers of the belt and being secured to the belt for holding the pump in place, the bulb protruding from between the layers through an opening in the outer layer and being movable between a relaxed configuration in which the bulb encloses a first volume of air and a collapsed configuration in which the bulb encloses a second volume of air smaller than the first;

conduit means extending from the bulb to said inflatable bladder means;

a valve disposed generally in said conduit means operable to permit fluid communication as the bulb is moved toward its collapsed position to force air from the bulb into said inflatable bladder means.

* * * * *

REEXAMINATION CERTIFICATE (3674th)

United States Patent [19]

Harrold

[11] B1 5,396,906

[45] Certificate Issued Nov. 24, 1998

[54] BACK SUPPORT BELT

[76] Inventor: David W. Harrold, 22167 Maretlla Ave., Boca Raton, Fla. 33433

Reexamination Request:
No. 90/004,436, Oct. 29, 1996

Reexamination Certificate for:
Patent No.: 5,396,906
Issued: Mar. 14, 1995
Appl. No.: 930,093
Filed: Aug. 13, 1992

[51] Int. Cl.[6] .................. A61F 5/37; A61F 5/00
[52] U.S. Cl. .................. 128/876; 602/19
[58] Field of Search .................. 602/5, 13, 19; 128/876, 878, DIG. 10, 96.1

[56] References Cited

U.S. PATENT DOCUMENTS

| | | | |
|---|---|---|---|
| 1,970,802 | 8/1934 | Johnson | 18/56 |
| 2,760,212 | 8/1956 | Gazelle | 9/19 |
| 4,348,774 | 9/1982 | Woodson | 2/338 |
| 4,682,587 | 7/1987 | Curlee | 128/78 |
| 4,682,588 | 7/1987 | Curlee | 128/78 |
| 4,789,202 | 12/1988 | Alter | 297/284 |
| 4,836,194 | 6/1989 | Sebsatian et al. | 128/78 |
| 4,905,993 | 3/1990 | Barone | 272/123 |
| 4,968,027 | 11/1990 | Anderson | 272/123 |
| 5,022,109 | 6/1991 | Pekar | 5/449 |
| 5,062,414 | 11/1991 | Grim | 128/68.1 |
| 5,088,478 | 2/1992 | Grim | 602/27 |
| 5,113,599 | 5/1992 | Cohen et al. | 36/88 |
| 5,144,708 | 9/1992 | Peakar | 5/454 |
| 5,152,302 | 10/1992 | Fareed | 128/878 |
| 5,155,866 | 10/1992 | Walker et al. | 2/18 |
| 5,158,767 | 10/1992 | Cohen et al. | 36/88 |

FOREIGN PATENT DOCUMENTS

0479014A1  9/1991  European Pat. Off. .

*Primary Examiner*—Michael Anthony Brown

[57] ABSTRACT

A back support belt having inflatable bladder members mounted on the inner surface of the belt to engage and support the lower back. A pump is further provided for inflating and deflating the bladder. The pump is integrally attached to the belt and includes a valve operable to permit inflation and deflation of the bladder, and a conduit for fluid communication between the pump, valve and the bladder.

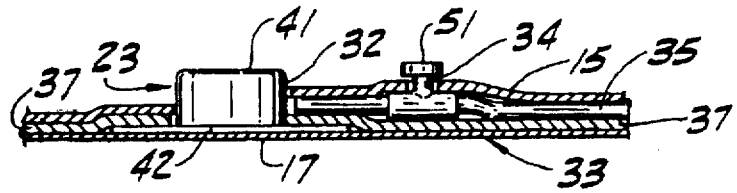

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–8 is confirmed.

New claims 9–10 are added and determined to be patentable.

9. *A back support belt comprising:*

*an outer layer;*

*an inner layer generally superposed with the outer layer, the outer and inner layers being sized and shaped for extending around the waist of the human body;*

*means for attaching opposite ends of the belt for securing the belt around the waist;*

*an inflatable bladder adapted to be disposed generally opposite the lower back of the human body for providing support to the lower back upon inflation of the bladder;*

*a pump comprising a base and a hollow bulb extending from the base, the base being sandwiched between the inner and outer layers of the belt and being secured to the belt for holding the pump in place, the bulb protruding from between the layers through an opening in the outer layer and being movable between a relaxed configuration in which the bulb encloses a first volume of air and a collapsed configuration in which the bulb encloses a second volume of air smaller than the first;*

*a conduit extending from the bulb to the inflatable bladder, the conduit being substantially unexposed as it extends from the bulb to the bladder; and*

*a valve disposed generally in said conduit operable to permit fluid communication as the bulb is moved towards its collapsed position to force air from the bulb into said inflatable bladder.*

10. *A back support belt comprising:*

*an outer layer;*

*an inner layer generally superposed with the outer layer, the outer and inner layers being sized and shaped for extending around the waist of a human body;*

*means for attaching opposite ends of the belt for securing the belt around the waist;*

*an inflatable bladder, adapted to be disposed generally opposite the lower back of the human body for providing support to the lower back upon inflation of the bladder;*

*a pump comprising a base and a hollow bulb extending from the base, the base being sandwiched between the inner and outer layers of the belt and being secured to the belt for holding the pump in place, the bulb protruding from between the layers through an opening in the outer layer and being movable between a relaxed configuration in which the bulb encloses a first volume of air and a collapsed configuration in which the bulb encloses a second volume of air smaller than the first;*

*a conduit extending from the bulb to the inflatable bladder, the inner layer having an opening therein to permit communication between the conduit and the bladder; and*

*a valve disposed generally in said conduit operable to permit fluid communication as the bulb is moved towards its collapsed position to force air from the bulb into said inflatable bladder.*

\* \* \* \* \*